(12) United States Patent
Blair et al.

(10) Patent No.: US 10,537,369 B1
(45) Date of Patent: Jan. 21, 2020

(54) BONE ANCHOR DEVICE

(71) Applicant: Medshape, Inc., Atlanta, GA (US)

(72) Inventors: Jeremy Blair, Atlanta, GA (US); Clay Williams, Atlanta, GA (US)

(73) Assignee: MEDSHAPE, INC., Atlanta, GA (US)

( * ) Notice: Subject to any disclaimer, the term of this patent is extended or adjusted under 35 U.S.C. 154(b) by 0 days.

(21) Appl. No.: 15/600,691

(22) Filed: May 19, 2017

Related U.S. Application Data

(60) Provisional application No. 62/339,077, filed on May 19, 2016.

(51) Int. Cl.
*A61B 17/68* (2006.01)
*A61B 17/72* (2006.01)
*A61B 17/00* (2006.01)

(52) U.S. Cl.
CPC .......... *A61B 17/7225* (2013.01); *A61B 17/68* (2013.01); *A61B 17/7266* (2013.01); *A61B 17/7283* (2013.01); *A61B 2017/00867* (2013.01)

(58) Field of Classification Search
CPC ............ A61B 17/7065; A61B 17/7258; A61B 17/7291; A61B 17/72–7291; A61B 2017/00867; A61B 2017/00871
See application file for complete search history.

(56) References Cited

U.S. PATENT DOCUMENTS

| | | | | |
|---|---|---|---|---|
| 7,052,498 B2 * | 5/2006 | Levy | ................. | A61B 17/7266 606/62 |
| 7,918,879 B2 * | 4/2011 | Yeung | ................ | A61B 17/0401 606/139 |
| 7,963,995 B2 * | 6/2011 | Richelsoph | ............. | A61F 2/442 606/90 |
| 9,498,266 B2 * | 11/2016 | McCormick | ....... | A61B 17/7291 |
| 9,545,274 B2 * | 1/2017 | McCormick | ....... | A61B 17/7291 |
| 2004/0230193 A1 | 11/2004 | Cheung | | |

(Continued)

OTHER PUBLICATIONS

Tacktill, Jordan Z and Powell, Donald R, "Hammertoe Implant Options" Podiatry Institute Update 2012; Chapter 14: 63-66 Online at http://www.podiatryinstitute.com/pdfs/Update_2012/2012_14.pdf.

(Continued)

*Primary Examiner* — Jacqueline T Johanas
(74) *Attorney, Agent, or Firm* — Morris, Manning & Martin, LLP; Bryan D. Stewart

(57) ABSTRACT

Provided herein are bone anchor devices including embodiments using adaptive materials, including shape memory materials such as shape memory alloys. Embodiments using shape memory alloys may use super-elastic properties of shape memory alloys to provide forces and deflections that actuate bone anchoring element(s) within bones. Embodiments of bone anchoring elements may be created that actuate with respect to one or more pivot point(s), with the bone anchoring elements on an opposite side of the pivot point from the actuating member composed of, for example, shape memory material. The pivot point(s) of a bone anchor device may be positioned in a central portion of the bone anchor device. The central portion of the bone anchor device may span between two pieces of bone or two separate bones (e.g., two bones of a joint) into which bone anchoring elements may be embedded and fixed.

8 Claims, 10 Drawing Sheets

(56) References Cited

U.S. PATENT DOCUMENTS

| | | | | |
|---|---|---|---|---|
| 2007/0233076 A1* | 10/2007 | Trieu | ............... | A61B 17/7065 |
| | | | | 606/249 |
| 2008/0114367 A1* | 5/2008 | Meyer | ............... | A61B 17/025 |
| | | | | 606/90 |
| 2011/0144645 A1* | 6/2011 | Saravia | ............ | A61B 17/1725 |
| | | | | 606/63 |
| 2015/0073413 A1* | 3/2015 | Palmer | ............ | A61B 17/7266 |
| | | | | 606/63 |
| 2015/0223848 A1* | 8/2015 | McCormick | ...... | A61B 17/7291 |
| | | | | 606/63 |
| 2015/0223849 A1* | 8/2015 | McCormick | ...... | A61B 17/7291 |
| | | | | 606/63 |
| 2015/0320460 A1* | 11/2015 | Taber | ................. | A61B 50/30 |
| | | | | 606/63 |
| 2016/0317198 A1* | 11/2016 | Fox | ................ | A61B 17/7225 |

OTHER PUBLICATIONS

Harms, Russell C, "Utilization of the X-Fuse™ Superelastic Implant for Hallux IPJ Arthrodesis XFHA3000 rev. A" Memometal Technologies Inc. Company, Memphis TN.

* cited by examiner

BONE ANCHOR DEVICE

RELATED APPLICATION AND PRIORITY CLAIM

This application claims the priority benefit of provisional application No. U.S. 62/339,077 filed May 19, 2016 entitled Bone Anchor Device, the disclosure of which is incorporated herein by reference for all purposes.

FIELD OF THE TECHNOLOGY

Embodiments of this disclosure relate to bone anchors for holding bones together under compression, including embodiments using shape memory materials, including super-elastic shape memory alloys.

SUMMARY OF THE DESCRIPTION

Provided herein are bone anchor devices including embodiments using adaptive materials, including shape memory materials such as shape memory alloys. Embodiments using shape memory alloys may use super-elastic properties of shape memory alloys to provide forces and deflections that actuate bone anchoring element(s) within bones. Embodiments of bone anchoring elements may be created that actuate with respect to one or more pivot point(s), with the bone anchoring elements on an opposite side of the pivot point from the actuating member composed of, for example, shape memory material. The pivot point(s) of a bone anchor device may be positioned in a central portion of the bone anchor device. The central portion of the bone anchor device may span between two pieces of bone or two separate bones (e.g., two bones of a joint) into which bone anchoring elements may be embedded and fixed.

In one aspect, the disclosure describes a bone anchor system including a bone anchor having a central portion disposed between at least two pivot points, and a distal anchor element and a proximal anchor element situated on the bone anchor. The bone anchor system includes an actuation control mechanism configured for holding the strain in the central portion of the bone anchor, thereby keeping the distal anchor element and the proximal anchor element in an aligned configuration. The actuation control mechanism is further configured such that a release of the strain in the central portion by manipulating the actuation controlling mechanism, thereby rotates one or more bodies of the bone anchor around the at least two pivot points, and thereby actuates the distal anchor element and the proximal anchor element simultaneously outward.

In another aspect, the disclosure describes a bone anchor system including a bone anchor for joining two bone pieces of one or more bones of a patient at an angle to an axis of the bone anchor, and at least two anchor elements each for extending into one of the two bone pieces of the patient, the at least two anchor elements rotationally connected via a connection spanning at least two rotational pivot points forming a central portion of the bone anchor. In the bone anchor, the central portion includes a shape memory alloy actuator made of a shape memory alloy with a selected austenitic finish temperature of the shape memory alloy selected such that the martensitic crystalline phases of the shape memory alloy are unstable at room temperature or far below body temperature (e.g., at 20 degrees Celsius). The at least two anchor elements are configured to be actuated about the at least two rotational pivot points away from the axis in response to a release of strain in the shape memory alloy of the central portion of the bone anchor. The bone anchor system further includes an actuation control mechanism configured for holding the strain in the central portion of the bone anchor and the actuation control mechanism is further configured such that a release of the strain in the central portion by manipulating the actuation controlling mechanism rotates the at least two anchor elements around the at least two rotational pivot points.

Other embodiments and features of the present disclosure will be apparent from the accompanying drawings and from the detailed description that follows.

BRIEF DESCRIPTION OF THE DRAWINGS

The embodiments are illustrated by way of example and not limitation in the Figures of the accompanying drawings in which like references indicate similar elements.

DETAILED DESCRIPTION

The following description and drawings are illustrative and are not to be construed as limiting. Numerous specific details are described to provide a thorough understanding. However, in certain instances, well-known or conventional details are not described in order to avoid obscuring the description. References to one or an embodiment in the present disclosure are not necessarily references to the same embodiment; and, such references mean at least one. Reference in this specification to "one embodiment" or "an embodiment" or the like means that a particular feature, structure, or characteristic described in connection with the embodiment is included in at least one embodiment of the disclosure. In the described several embodiments, like features (although they need not be identical nor same embodiment) are noted with the same numerical designations. The appearances of the phrase "in one embodiment" or the like in various places in the specification are not necessarily all referring to the same embodiment, nor are separate or alternative embodiments mutually exclusive of other embodiments. Moreover, various features are described that may be exhibited by some embodiments and not by others.

Figure 1:
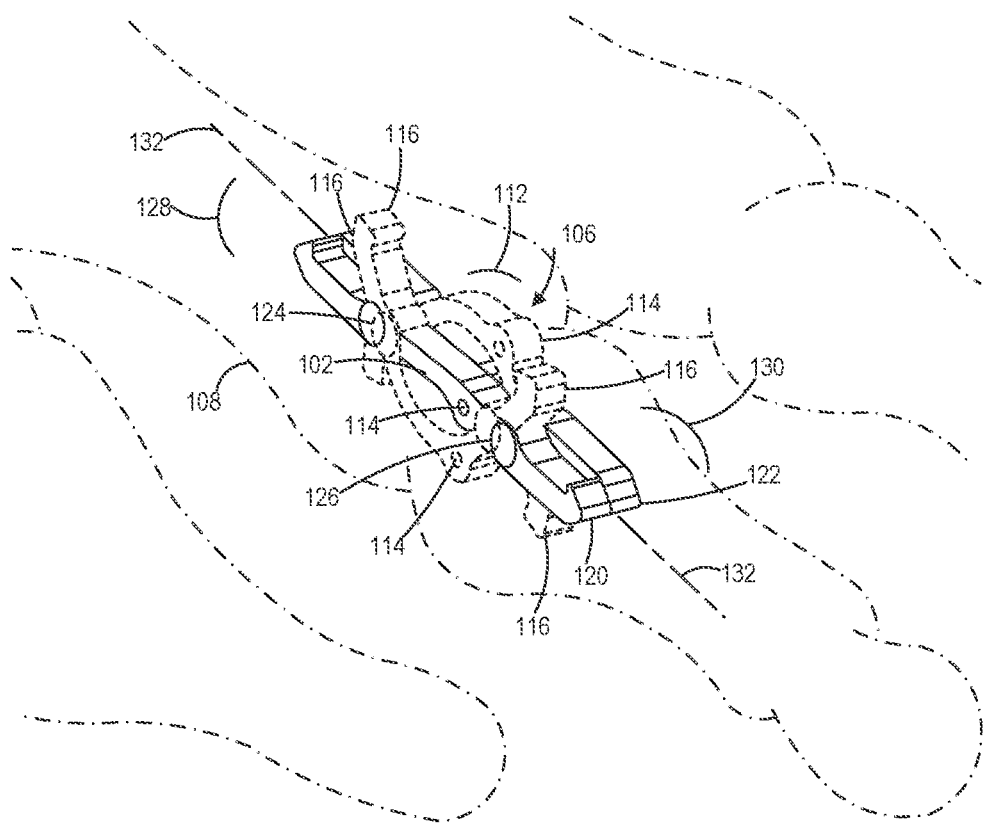
FIG. 1 shows an exemplary embodiment of a placement of a bone anchor device as described herein in both its insertion shape and deployed shape.

FIG. 1 shows an exemplary embodiment of a placement of a bone anchor device 100 as described herein in both its insertion shape 102 and deployed shape 104. The device is shown configured and positioned in bores made in bones of a patient's foot at the proximal interphalangeal (PIP) joint 106 that has been prepared for fusing. For example, the two bones of the PIP joint 106 may be fused to alleviate the symptoms of hammer toe. In that example, the two bone pieces being fused in this embodiment are the proximal phalanx 108 and the middle phalanx 110 of the human toe. Other bones or bone pieces may be fused with similar devices to those disclosed herein, including pieces of fractured bones or other attachments to bone.

In the example of the device 100 shown, the proximal phalanx 108 and the intermediate (middle) phalanx 110 are joined by pulling each bone piece toward the other during and after deployment of the device using the device's arms at the prox. Deployment of the device 100, as described further herein, includes engaging and drawing each bone piece (108 and 110) toward the other, toward a central portion of the device 112 (e.g., along an axis of the device, at an angle to the bone interface). In some embodiments described herein, the bone device guides the bone pieces to interface at an angle, an angle that can be matched to an axis or axes of the anchor elements on the device. The surgical preparation of the bone pieces before fusing also can influence the angles at which the device joins the bone pieces.

In the embodiment of the device 100 shown, the interface is a prepared joint between the proximal phalanx 108 and the middle phalanx 110. Other preparations of the bone pieces may be made to facilitate joining of the two bone pieces. The interface may be adapted to temporarily accommodate a deployment pin or other deployment mechanism between the bone pieces. Similarly, the bone device may be adapted to conform to other aspects of the bone pieces intended to be fused. For example, different embodiments described herein show different placements of a pinhole (shown in this embodiment as pinhole 114) with respect to the arms and pivot points of different devices and the effects of these changes on the device deployment into the bone pieces.

In the embodiment of the device 100 shown, the device has two arms 120 and 122 moving against each other that are joined at two pivot points, a proximal pivot 124 and a distal pivot 126. These two arms form two paired "wings" portions 116 on both the proximal end of the device 128 (e.g., adapted to be deployed in the bone piece nearer to the patient's heart) and the distal end of the device 132 (e.g., adapted to be deployed in the bone piece further away from the patient's heart). In the embodiment shown, the distal end of the device 130 is adapted to be deployed in the intermediate phalanx 110 of the human toe and the proximal end 128 is adapted to be deployed in the proximal phalanx 108. As described further herein, the "wings" portions 116 of the arms 120 and 122 at each end of the device are adapted to engage the cortical layers of the respective bone pieces and to deploy after a pin is removed from the device along the bone interface between the two bone pieces. This pin is engaged with the device via a pinhole 114 on the device that is positioned as described further herein, based on the unique requirements of the bone pieces. For example, the dimensions of the middle phalanx 110 of the human toe dictate that certain embodiments are adapted for particularly small bone pieces, including relative lengths of the arms 120 and 122 and their "wings" portions 116 as described further herein.

Embodiments described herein show the release of strain that is already activated for recovery in the central portion 112 of arms of the device. For example, the materials of the arms of the device may be formed of a material that is already activated to recover stored strain immediately upon removing the pin or other constraint from the device 100. In other words, for shape memory alloys, the alloys described herein are described as having an austenite finish temperature below (e.g., well below) the insertion temperature, and thus the strains stored by the device (e.g., stored as temperature-unstable stress-induced martensite structures) are consistently activated for recovery at the storage and insertion temperature. Therefore, although shape memory alloys (and shape memory materials in general) are described herein, their properties related to storing a memorized shape are not being used by the devices described herein. Rather, the shape memory alloy of the devices described herein is being used for its pseudo elastic (or super elastic) properties such as being able to store significant strains with high moduli and to provide immediate recovery of these strains to create a very rapid deployment of the device.

However, the range of embodiments of devices described herein are not limited to using a shape memory alloy in the central portion 112 of the arms 120 and 122. Other materials can be used to store strain and deploy the wings 116 of the device immediately (e.g., within a small portion of a surgical time period) within the bone pieces 108 and 110. For example, elastomers or other polymers may be used. Other arrangements of pivot points may be adapted to include other materials in the central regions of the arms. Other central portion geometries or arrangements of pivot points may be adapted in order to use these different materials.

Other embodiments may use other deployment mechanisms or strain release mechanisms. For example, a clamp (e.g., a forked tool) may be similarly used to constrain the two arms from the outside before deployment. As another example, a clamp and a pin/pinhole system may be combined. Other interlocking deployment mechanisms may be used and adapted for use with the various embodiments described herein that use a deployment pin for deployment.

Figure 2:
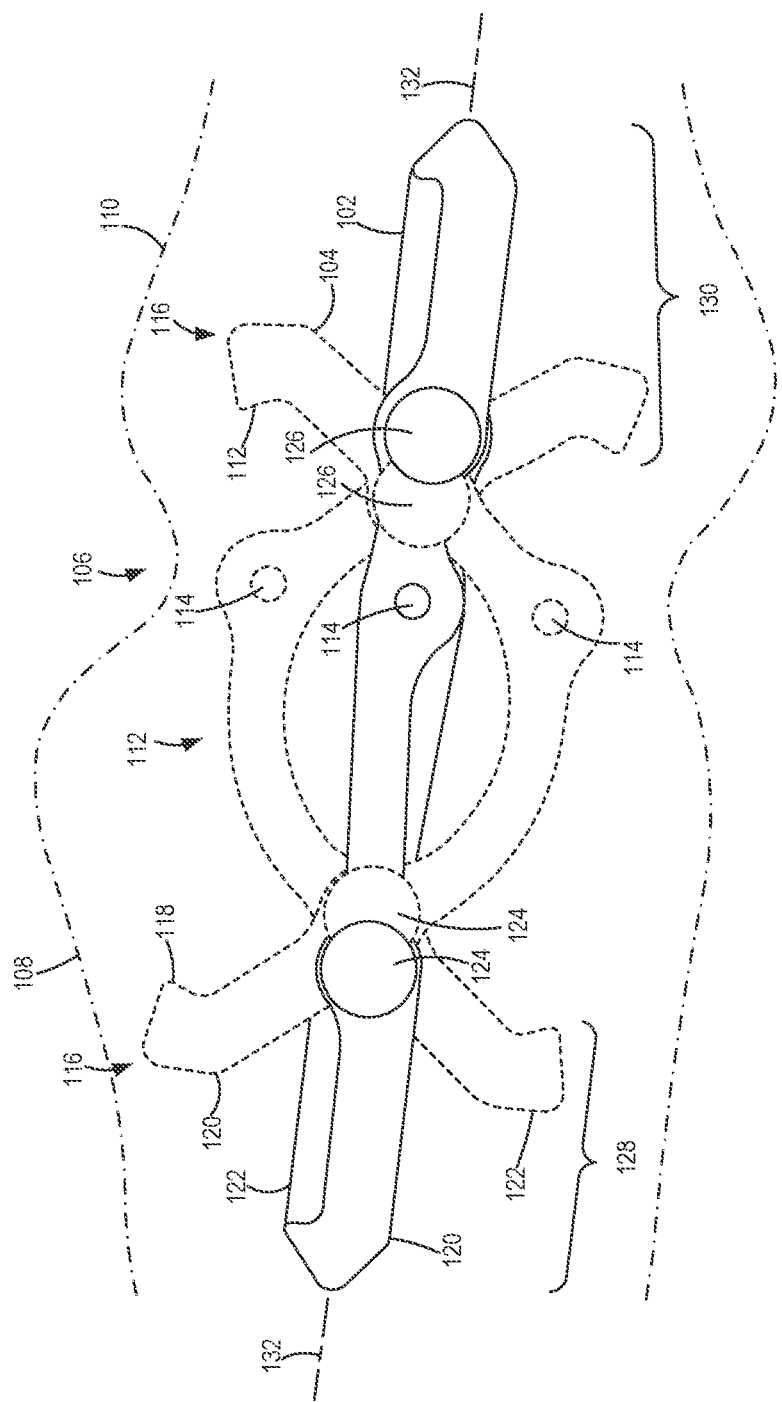
FIG. 2 shows an embodiment of a bone anchor device in both an insertion shape (e.g., a straightened strained state) and a deployed shape (e.g., an actuated and deployed state).

FIG. 2 shows an embodiment of a bone anchor device 100 in both an insertion shape 102 (e.g., a straightened strained state shown) and a deployed shape 104 (e.g., an actuated and deployed state). In the embodiment shown, the device is a double armed body attached at two pivot points, a proximal pivot point 124 and a distal pivot point 126. A pinhole 114 for receiving a deployment pin is placed through each arm of the body such that straining the arms 120 and 122 (e.g., between the two pivot points 124 and 126) causes the pinholes 114 in each arm to overlap in the insertion shape 102 (e.g., the straightened shape). A deployment pin or other body is used to hold the pinholes in alignment, and thus the arms in a strained position comprising the insertion shape 102. By removing the pin or other body from the pinhole, the arms 120 and 122 are allowed to recover the strain stored in the strained insertion shape 102 and to attain a deployed shape 104 after recovering at least a portion of that strain. In the view shown, the axis of the pinhole 114 is orthogonal to the plane of the page, and, for example, any deployment pin used for restraining the device from deployment is moved into or out of the plane of the page.

The pivot points 124 and 126 of the exemplary device 100 may be made in any manner. Though illustrated in the embodiment shown as pivot pins engaging pivot pinholes 124 and 126, the pivoting points between the two arms may be formed in other manners. For example, other manners of joining two scissoring bodies may be employed, include ball joints or other moving, locked, and pivoting arrangements.

The bone anchor device 100 described herein may be adapted to deploy its arms 120 and 122 immediately upon removal of a pin or other body from a pinhole 114. For example, this may be due to an activated (but not yet recovered) stored strain, such as from a shape memory alloy above a martensitic finish temperature, or a shape memory polymer above a glass transition temperature, or from an elastomer or other body that can store and recover a significant percentage of strain. For example, due to the device being above a recovery temperature when the pin is removed, removing the deployment pin or other element from a pinhole 114 while the device is in its insertion shape 102 (e.g., straightened state) causes the device arms to recover their stored strain and to deploy immediately.

The embodiment of the device 100 shown has been adapted for the particular bone pieces shown, namely the phalangeal bones of the human foot 108 and 110. Other devices may be adapted for connecting or fusing other bone pieces. Such adaptations can concentrate stresses across the interface with the deployment pin and pinhole of the device during insertion and deployment. This can affect the ability to install the device properly within two bone pieces because the deployment process can move the device based on the forces required to cause deployment. For example, removing a pin from a pinhole 114 can have significant friction forces on the pin (or other element inserted into the pinhole) that can cause movement of the device relative to the bone pieces 108 and 110 during deployment. Therefore, as described further herein, the design of shapes of the device 100 and the device's deployment design are linked.

As described further herein, the combination of having restoring forces activated on the arms 120 and 122 and moving a deployment pin or other object out of a pinhole 114 creates additional forces that need new devices/methods to maintain accurate placement and deployment of the device 100 within the bones 108 and 110 during surgery. Some of these new devices/methods relate to the bone anchor device 100 and some relate to the deployment apparatus for actuating a constraint on the device 100 (e.g., removing the pin from the device's pinhole 114).

Proper removal of constraints on the device's arm 120 and 122 (e.g., removal of a pin from the pinhole 114) does not disturb the device or bone construct significantly, allowing the surgeon to position and deploy the device accurately in the prepared PIP joint 106. Direct access from outside the bone to the pinhole 114 greatly simplifies and eases the process for removing a constraint from the device 100. When removed, the constraint will be limiting movement of arms 120 and 122 while they are at the same time producing significant restoring forces to recover the imparted strain, and thus significant forces that could move the device 100 out of desired alignment. A device 100 that deploys immediately with these large restoring forces can require direct access to the pinhole 114 until the time of deployment, such as at a bone interface within the PIP joint 106. In several embodiments, therefore, devices are described herein that include the pinhole 114 located in an area of an expected bone interface. Another advantage of accessing the pin and pinhole 114 at the interface of the two bone pieces (e.g., PIP joint 106) is that limited or no additional bone removal is required for actuating the device beyond the proper insertion of the device and reduction of the bone construct/interface.

By adjusting the design of the placement of the pivot points, 124 and 126, and the deployment pinhole 114, the device 100 may effectively locate the deployment action of the wings (e.g., the length of the "wings" portions on the ends of arms 120 and 122) with respect to the bone interface 106 and within the two bone pieces 108 and 110. As described further herein, the wings portions 116 may include teeth 118 or ridges designed for engaging cortical layer(s) of bone in the particular bone pieces being fused and the length/shape of the wings may be adapted to engage the cortical layers of bone while otherwise fitting within the bone piece and allowing practical deployment of the device from within the prepared bone joint (e.g., interface between bone pieces).

In an embodiment where the bone pieces are fractured pieces of a long bone, the bone anchor device embodiments herein may be designed to help fuse the fracture site (which may be prepared) and the device elements may be adapted to conform to use with those particular bone pieces. In some embodiments, a fracture may include a joint that is also being fused with the other bone piece. For example, a fractured bone piece may include a joint and/or the joint could be advantageously fused with a bone piece that is not a part of the joint (e.g., adjacent to the joint).

Alternatively, bone pieces may be fused with bone interfaces that are distracted such as via various spacing constructs. For example, a bone implant (e.g., treated bone tissue) may be used to space or fill a bone interface allowing the bone pieces to be fused using the bone anchor in a position other than the natural positioning of the bone pieces, which may be fractured bone pieces. For embodiments using a spacing construct, the bone interfaces would transmit the fusing forces of the device through the spacing construct. Further, the placement determinations before and during deployment of the devices described herein may apply to any spacing constructs and all of the areas between the two bone pieces. For example, direct access to the constraints on the arms remains an important design consideration, although one or more spacing construct(s) may provide additional options for this access.

Using these embodiments of the bone anchor device and deployment methods described herein creates novel requirements for the device 100 itself, particularly for the placement of the deployment pinhole 114 and positioning the device when inside the created bone tunnel. For example, designing the placement of the pinhole 114 off the center of the central portion 112 of the device 100 along the device axis (nearer to one of the pivot points) has the effect of moving the intended placement of the bone interface 106 relative to the device axis due to this embodiment's use of the bone interface as access during surgery (e.g., for a deployment tool). The embodiment locates the pivot points 124 and 126 relative to the bone pieces 108 and 110 at the time of deployment, thus further modifying the motion of the deployment of the wings portions 116 with respect to layers of bone within the bone pieces.

While deploying the forces exerted by and on the device 100 can move the device, shifting the inserted position and/or the deployed position of the device within the patient's bones 108 and 110. This potential movement can severely limit the efficacy of the deployed device. As introduced above, removing a deployment mechanism (e.g., a pin) from the pinhole 114 while the central portions 112 of the arms 120 and 122 are activated to change shape (e.g., rotate to deploy the wing portions 116, bend the central portions of the arms, recover stored strain in the central portions) can cause both torsion and translation of the device relative to the bone pieces, including during the insertion procedure, and during the process of removing the pin or otherwise allowing the device to deploy.

In the embodiment of the device 100 shown, in its insertion shape 102 (e.g., in its straightened shape), the bone anchor device stores strain in the central portion 112 of each of its arms 120 and 122, shown straightened such that the pinholes 114 in each of the arms aligns. As described further herein, in order to create additional strain in the insertion shape, the pinholes 114 in each arm are positioned off-center (e.g., up or down) with respect to a central axis 132 of the arms 120 and 122, thus requiring the centers of the arms to cross in order to align the pinholes 114 of each arm. This allows each arm 120 and 122 to be strained further (e.g., store more strain) than when the pinholes 114 are aligned with the central axis of the arms. As shown in the embodiment of the device In some embodiments described further herein, this additionally-strained position of the arms 120 and 122 will align the off-center pinholes 114 with another line or axis between the pivot points 124 and 126, which may be different from the central axis 132 of the arms.

Therefore, the term "straightened" as used herein with respect to the arms of the device 100 is meant only to refer to an embodiment with a straight axis, such as for a straight insertion shape 102 and/or as desired for interfacing the bone pieces once fused. For example, a bone device may interface the bone pieces at an interface angle. In some embodiments, the desired interface angle or desired device angle (either as inserted or as deployed), may include an angle deviating either from straight or normal/orthogonal angles. The desired angle may include a desired angle for a fused joint, or a desired angle for fusing a bone fracture (e.g., of a long bone). A preferred angle for the bone interface or device may be included in a strained shape and/or in a deployed shape of the embodiment of the device. For example, one angle (e.g., of the bone interface) may be determined or enforced by one shape of the device (e.g., insertion shape) and another angle may be determined or enforced by another shape of the device (e.g., deployed shape).

Figure 3:
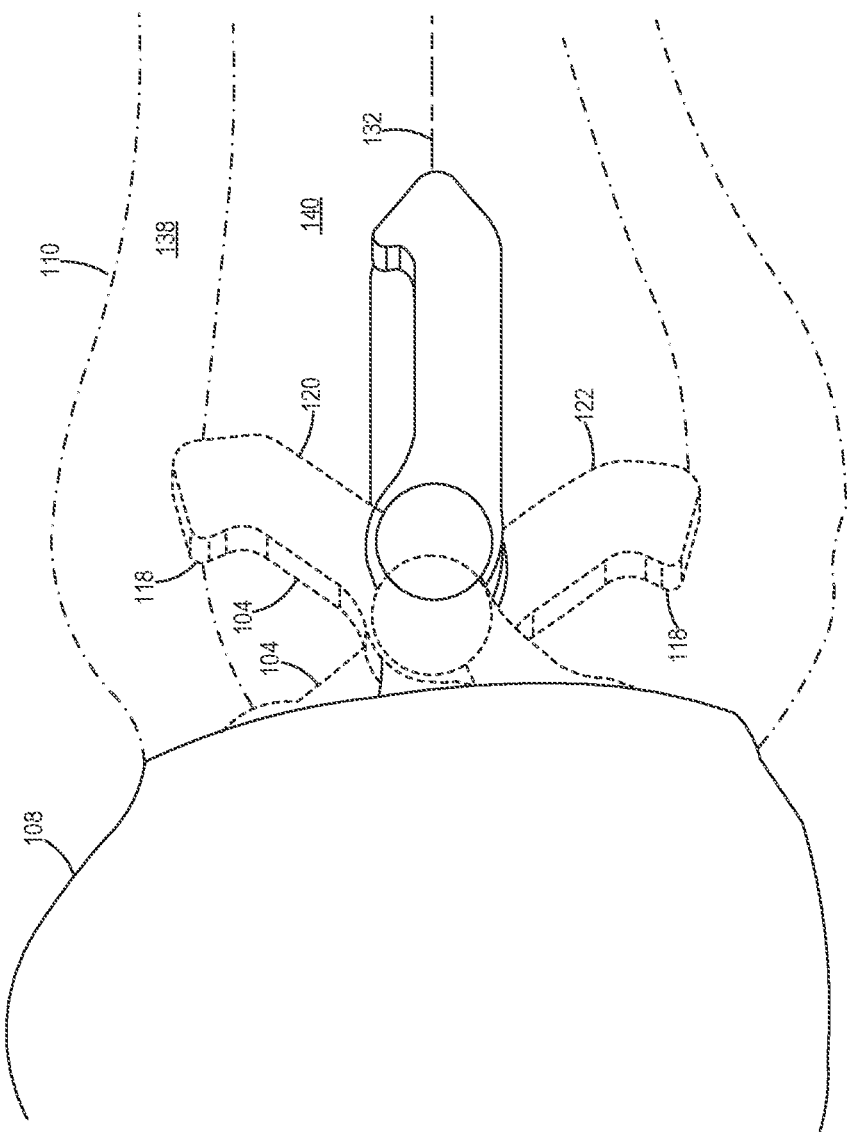
FIG. 3 shows details of an embodiment of a bone anchor device with its wings portion as installed in the intermediate phalanx.

FIG. 3 shows details of an embodiment of a bone anchor device 100 with its wings portion 116 as installed in the intermediate phalanx 110. Device 100 is shown in both an installation shape 102 (e.g., a straightened strained state) and an actuated and deployed shape 104, showing details of bone pieces 108 and 110 with cortical bone portions 138 and cancellous (or trabecular) bone portions 140 engaging with the bone anchor device. The device 100 is shown within a model of a human phalanx with a prepared joint positioned for fusing. The model of bone pieces shows a slight curvature in the boundary between the cancellous bone 140 and the cortical bone 138, curving toward the central axis 132 of the device 100.

In embodiments described further herein, the device's wings portions 116 may be designed with particular dimensions and shapes of the wings portions. These designs may adjust the engagement of the wings of the device in its deployed position, including any "teeth" shapes 118 (e.g., bumps or ridges) with the cortical layer 138 of the bone. Many embodiments of the design of the wings portion 116 are described herein for application to different bone pieces, including different sizes of bone, bone shapes, and shapes of cortical bone layers 138. As described further herein, other changes in the device design may be made for maintaining accurate placement and deployment for in a particular surgical application.

For example, in the embodiments shown for fusing the PIP joint 106 may be used to alleviate severe cases of joint deformity (e.g., hammertoe) by either completely straightening the joint or fusing it at a reduced angle. Surgery may be used to correct one or more joints on a patient, or to fuse one or more bone pieces, and the desired outcomes of each of these bone interfaces may be orthogonal, or at an angle. In the embodiment shown with the specific bones of the PIP joint 106, the intermediate phalanx is a particularly short bone into which the distal end 130 and its wings portion 116 need to be deployed. These particular bones therefore require specific adaptations to the device 100 and its wings portions 116 to engage the cortical layer effectively.

Different bones pieces will have different configurations of harder and softer bone tissue (e.g., cortical bone 138 and trabecular or cancellous bone 140). To enhance pull out strength along a central axis 132 of the device 100 (or another axis), the wing portions 116 of the device may be designed both to engage the cortical bone layer 138 (e.g., compress other bone tissue against the cortical layer) while in its deployed shape 104, and also to fit well within the bone pieces in its insertion shape 102 during the insertion process of the device. The preparation of the bone pieces may also affect the cortical layers of the bone pieces particularly at the insertion and deployment sites. Therefore, the PIP embodiment of the device 100 described herein is adapted to adjust the deployed shape and the insertion shape to fit and to fuse the particular bones of the described prepared PIP joint 106. However, the adaptations designed for these bones may be usefully adapted to different configurations for a variety of bone pieces.

Figure 4:
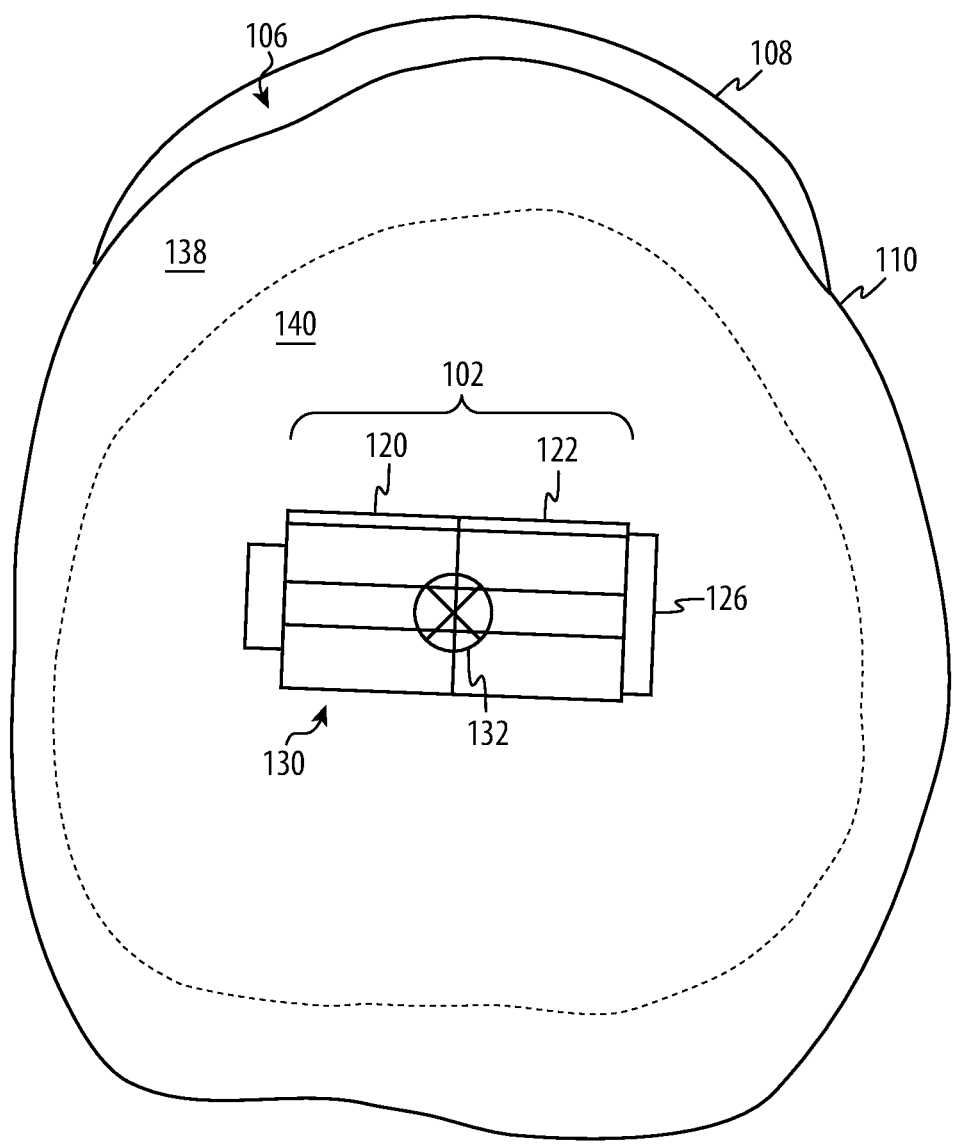
FIG. 4 shows an exemplary embodiment of a bone anchor device placement within bone piece across a prepared joint while in its insertion shape, with a device axis (orthogonal to the drawing plane).

FIG. 4 shows an exemplary embodiment of a bone anchor device 100 placement within bone piece 108 and 110 across a prepared joint 106 while in its insertion shape 102, along a device axis 132 (orthogonal to the drawing plane). This view shows cancellous/trabecular bone 140 and cortical bone 138 portions and the device 100 in an undeployed or insertion shape 102. In the embodiment shown, the device 100 is designed with two moveable arms 120 and 122 locked together in pivoting arrangement around pivot points 124 and 126, described further herein and shown here with horizontal rotational axes. This arrangement of pivot points 124 and 126 creates a significant horizontal dimension that does not move (e.g., orthogonal to the main vertical dimension of actuation of the wings portions 116), while the vertical dimension (e.g., height) of the device 100 is the dimension along which the device deploys. Deployment in this vertical dimension is discussed further with respect to FIG. 5.

Figure 5:
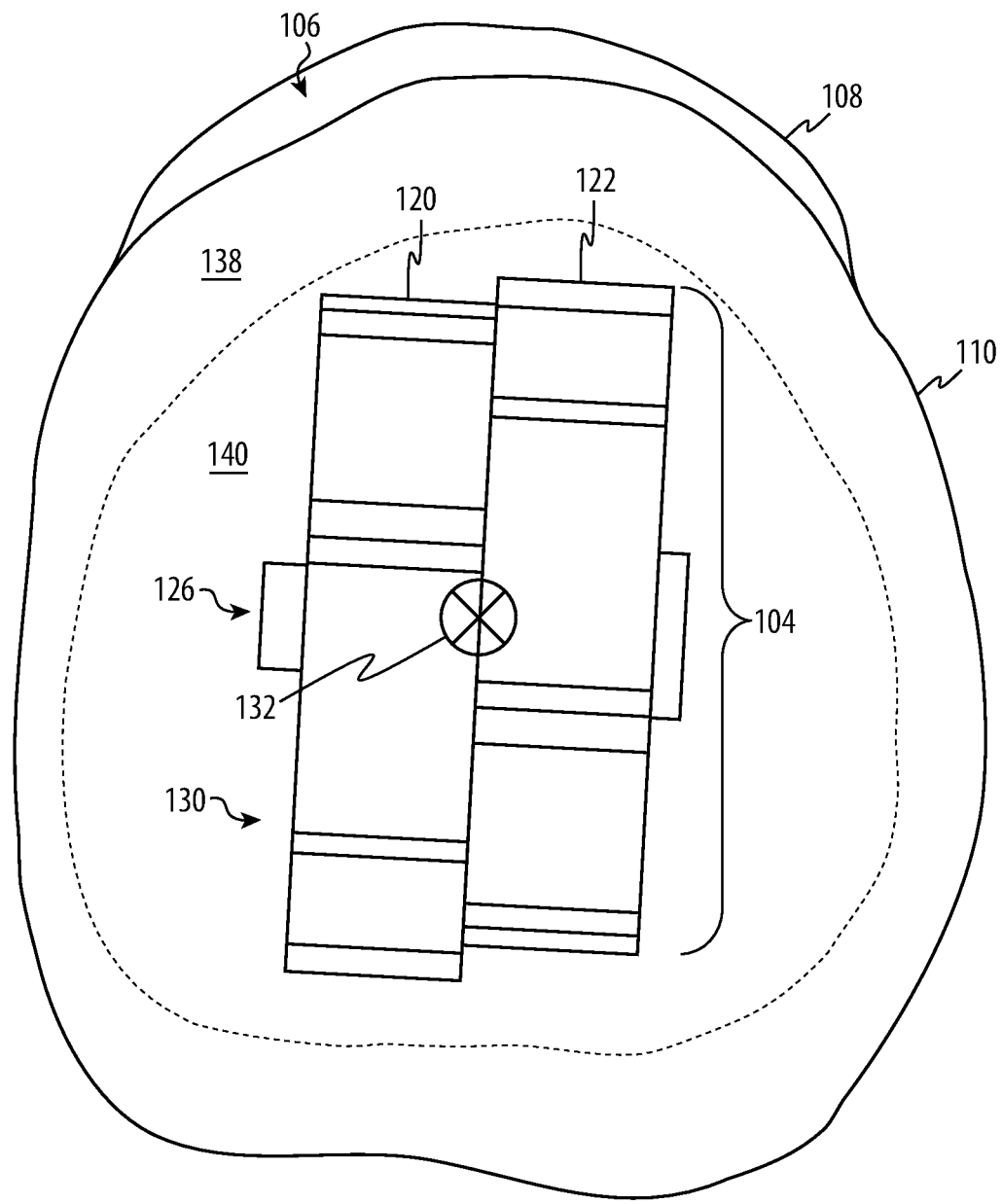
FIG. 5 shows an exemplary embodiment of a bone anchor device within bone pieces across a prepared joint shown along a device central axis while the device is in a deployed shape.

As shown in both FIG. 4 and FIG. 5, the insertion shape 102 and deployment shape 104 of the device may be both designed for the device's use in a particular bone piece (e.g., proximal phalanx 108 and intermediate phalanx 110). For example, the device shown has significant width at the points where the arms are connected. This width does not expand or provide additional engagement of the bone during deployment. However, this width dimension must be fit within the bone and may not be able to be reduced due to different device constraints (e.g., mechanical bending strength of the device, torsion rigidity of arms 120 and 122). For example, the pivot point structures must provide sufficient rigidity to provide ease and accuracy of both the insertion and deployment of the device, as described further herein.

Therefore, the three-dimensional device 100 must be fit to, and function within, the particular bone piece, both as the device is inserted and as deployed. This particular fitting leads to innovative adaptations of the devices in order to develop the necessary pull out strengths and mechanical bending and torsion strength of the device within the tight confines of small bone pieces such as the intermediate phalanx. In one embodiment, the device's central axis 132 in the inserted state may be aligned with an axis of the bone piece, each as shown normal to the plane of the Figure. In another embodiment, the device axis may be translated and/or rotated relative to the bone piece from the configuration shown, changing the margins of cancellous bone 140 through which the device will deploy before reaching cortical bone layers 138.

Further, the surface(s) of the bone interface, which may be parallel, near parallel or at an angle to the plane of the image in the Figure, may be translated along a central axis 132 of the device by modifying the design to adapt to deployment in different bone pieces by adjusting the deployment of wings portions. These adjustments in design are described further herein. Controlling the insertion shape 102, the deployed shape, and how the device behaves during insertion and deployment processes are critically important for installing devices with these large deployment forces into small bone pieces. The adaptations to the device and deployment tools/techniques create new device designs and novel deployment methods, described further herein for the several embodiments.

FIG. 5 shows an exemplary embodiment of a bone anchor device within bone pieces 108 and 110 across a prepared joint 106 shown along a device central axis 132 while the device is in a deployed shape 104. This view shows the deployed shape 104 as having moved the wings portions 116 of the device through the cancellous bone tissue 140 and toward the cortical bone tissue 138 in the bone piece.

The spatial arrangement illustrates an embodiment exemplifying that different sizes of bone pieces 108 and 110 will require specific deployment properties of the device, properties that make the developed compressive force (e.g., or a relative pull out force) substantial once the device is deployed in the bone pieces. This lever action of deployment shows a significant vertical displacement of the wings 116 into the cancellous bone 140, compressing and otherwise deforming that tissue and possibly engaging the cortical bone layer 138. The interaction of the wings 116 with both types of tissue 138 and 140 depends on factors like the shape and length of the wing and the device's placement before deployment, such as the alignment of the device axis 132 (or axes, such as in an angled device embodiment described further herein) and the placement of the device within the bone interface (e.g., prepared joint 106).

The actions of insertion and deployment of the device 100 within the bone pieces 108 and 110 provide a set of three-dimensional placement decisions for both the device designer and surgeon that involve design of both the insertion shape and the deployed shape of the device, as well as a surgical techniques and tools for deploying the device 100 in a patient's particular bone pieces 108 and 110. Therefore, described below are further details of deployment tools adapted for deploying exemplary deployment pins from pinholes 114 under significant forces (e.g., friction between pin and pinhole) developed by the device arms 120 and 122 while they are activated for deploying.

As described further herein, the exemplary embodiment of two arms connected by pivot points 124 and 126 to two pairs of wings portions 116 creates a device 100 with a simple scissor action between the central portion of the arms 112 and the two sets of wings, which may each include a straight wing section with a tooth or other engaging feature.

Other lever or pivot point arrangements can be adapted for use instead of the described pivot points using a reinforced pin and pivot pinholes in the wings. For example, these other embodiments of pivot points may be adapted for use with alternate materials or mixed materials. The effect of these alternate pivot points on the wings may multiply or alter the lever action of the wings portions 116 upon deployment (shown in the Figure in the vertical dimension). As described further herein, this length of the wing portion 116 can be adjusted with respect to placement of the pivot points 124 and 126, and with respect to the bone interface (e.g., a prepared PIP joint 106), allowing a device design to trade insertion and deployment characteristics of the device by moving the deployment pinhole 114 and arm pivot points within the device's design.

Figure 6:
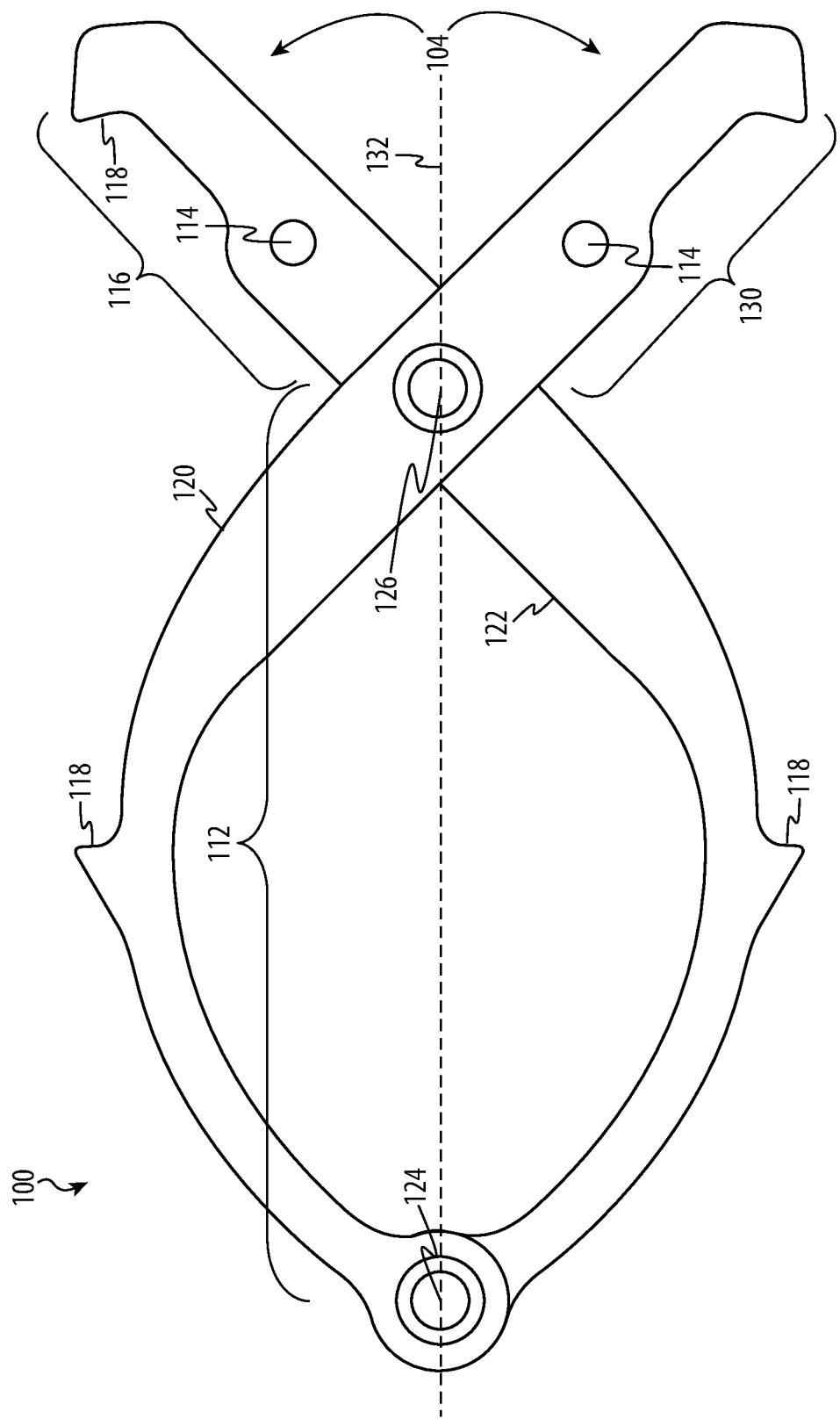
FIG. 6 shows an exemplary embodiment of a bone anchor device with pinholes on a wing portion of the arms while the device is in its deployed shape.

FIG. 6 shows an exemplary embodiment of a bone anchor device 100 with pinholes 114 on a wing portion 116 of the arms 120 and 122 while the device is in its deployed shape 104. This embodiment of the device 100 allows further movement of the bone interface for fusing along the central axis of the device (e.g., proximally/distally). Specifically, the embodiment shown allows the bone interface between bone pieces to be placed somewhere along the wings portion 116 of the undeployed device, rather than having to be placed in a central portion 112 of the device. In this arrangement, the device 100 allows deployment with both device pivot points 124 and 126 within one bone piece, which may be useful for embodiments where one bone piece is small or much smaller than another. For example, the device end with the wings portion 116 (e.g., distal end 130) may be placed in a particularly small bone, allowing the bone interface (e.g., as aligned with pinholes 114) to be placed on the device outside of the central portion 112, beyond the two pivot points, thereby enhancing the deployment action of the wings portion within the smaller bone piece.

This embodiment further shows a device 100 with only one set of wings portions 116 extending beyond the pivot points on one side (proximal or distal). In this embodiment with only one wings portion 116, teeth 118 or other bone-fixing features may be placed on the central portion 112 of the device. In another embodiment, teeth may be added to the central portion 112 of the device even if there are two wings portions for the device 100. Further, a design with only one wings portion 116 may create torsion load or stress around the central axis 132 of the device 100, around another portion of the device, between bone pieces, and/or rotating one bone piece relative to the other. This torsional load can be mitigated with other design adaptations, including teeth or wings described herein. Alternatively, such an unbalanced design with a wings portion 116 on only one end of the device 100 may be used for only particular applications.

Certain elements of this embodiment may be advantageously used without using all of the elements described herein. For example, placing a pinhole 114 for deployment outside the central portion 112 of the device 100 can be incorporated into other embodiments with wings portions 116 on both sides of the pivot points. Advantages of placing the pinhole 114 outside of the central portion 112 between two pivot points 124 and 126 include allowing placement of the bone interface outside both pivot points and/or placement of two pivot points inside one bone piece, and allowing the bone interface to include the deploying wings (e.g., for particularly short bone pieces), such as shown by the expanding action of the wings portion 116 at the bone interface (e.g., aligned with pinholes 114).

Figure 7:
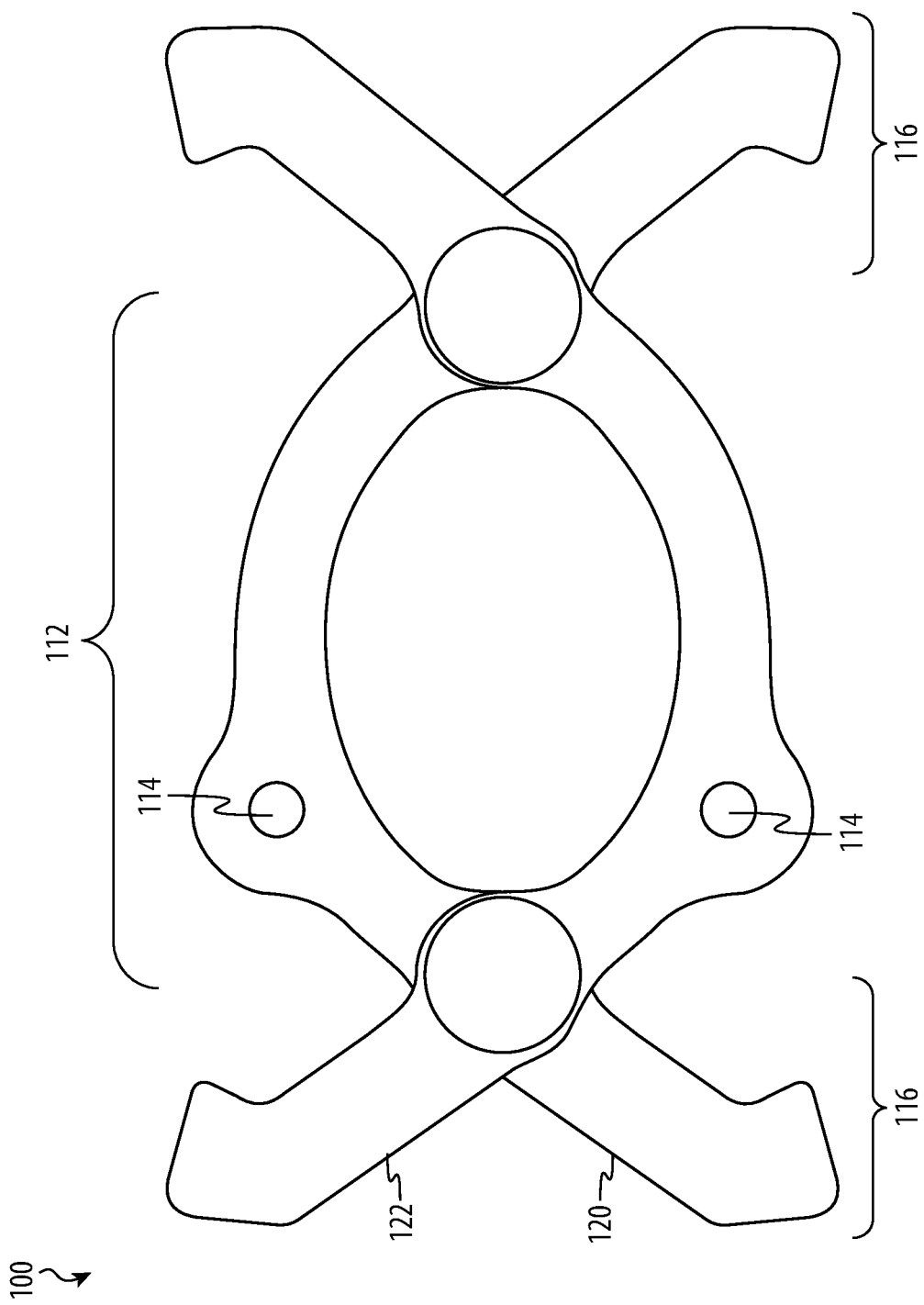
FIG. 7 shows an exemplary embodiment of bone anchor device with pinholes in central portions of the arms that are placed off a central axis of the arm in order to provide over-straining (e.g., over-compression) of the central portions of the arms when the pinholes are aligned.

FIG. 7 shows an exemplary embodiment of bone anchor device 100 with pinholes 114 in central portions 112 of the arms 120 and 122 that are placed off a central axis of the arm in order to provide over-straining (e.g., over-compression) of the central portions 112 of the arms when the pinholes 114 are aligned. A compressed form of an arm 120 or 122 with a similar configuration provides over compression by requiring alignment of pinholes while the center portions of the arms have already passed each other. This is a similar off-axis configuration to the arm configuration shown in FIG. 2, with the strained arms showing strain above a central axis defined by the pivot points.

In alternative embodiments, the pinhole may be offset differently than shown, such as, for example, by using a bent central arm portion or a bent wing portion that requires that the arms pass each other before the pinholes 114 of each arm align. Also, as described further herein, other embodiments of restraints may allow overstraining, or the rotation of the arms 120 and 122 or wings portions 116 thereof to be extended in other ways apart from modifying the placement and alignment of deployment pinholes 114.

Figure 8:
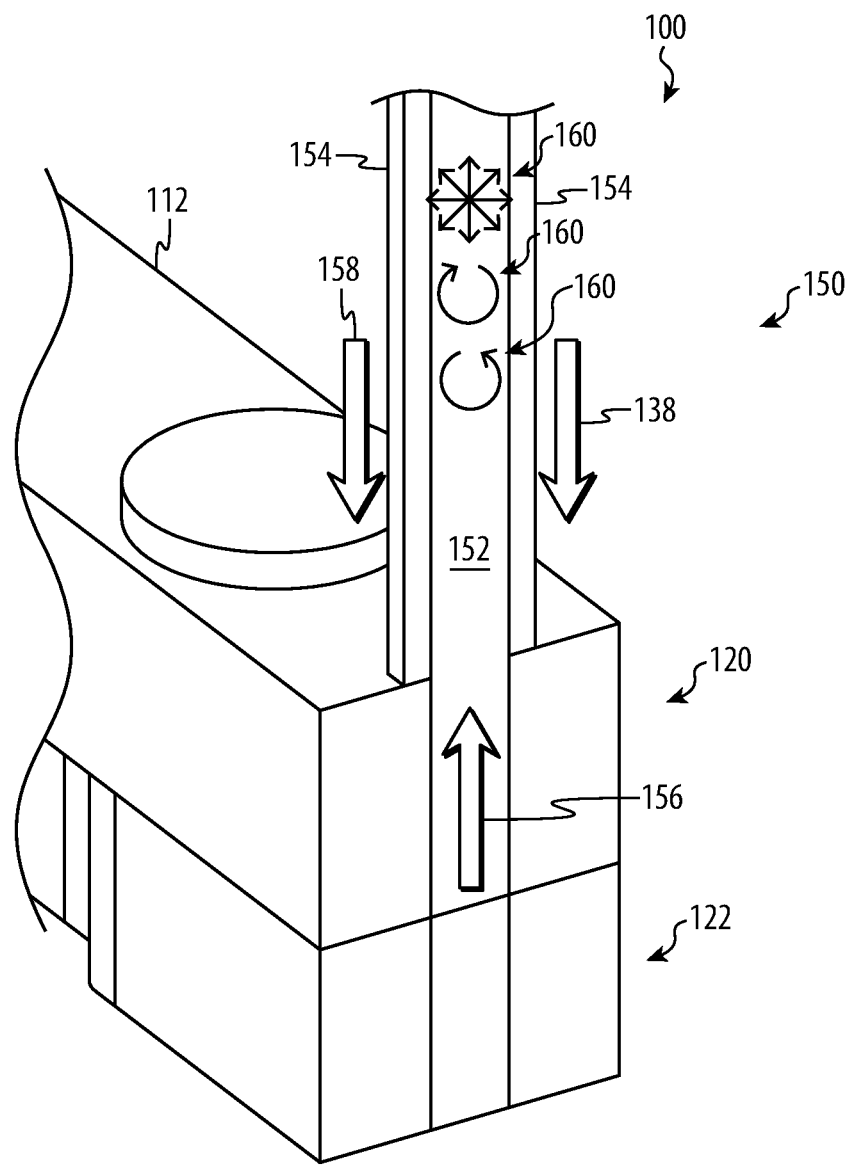
FIG. 8 shows an exemplary embodiment of a composite sheathed deployment pin mechanism.

FIG. 8 shows an exemplary embodiment of a composite sheathed deployment pin mechanism 150. The exemplary embodiment shows how forces are used for removing a central deployment pin 152 that is contained within the sheath 154. The movement of the deployment pin 152 from within the strained arms 120 and 122 of the device 100 can move the device if the restoring forces generated by the arms are significant due to the stored strain therein. For example, the restoring forces will be significant where the central portion 112 of the arms 120 and 122 are a shape memory alloy that has been super-elastically strained into a straightened configuration. As shown by the upward-pointing arrow 156 over the deployment pin 152, in this exemplary embodiment, the deployment pin 152 may also require a significant force to overcome the friction on the pin from the pinhole 114. In this exemplary embodiment of a dual pin design, while the deployment pin 152 moves upward, the pin sheath 154 (e.g., a second pin outside of or adjacent to the deployment pin) is pressed downward, providing a countering downward force as shown by the downward arrows 158 along the pin sheath 154.

The embodiment shown of the sheathed deployment pin mechanism 150 is only one embodiment of a dual-pin design from which a number of different embodiments may be created that utilize the fundamental push and pull forces 156 and 158 on the bone anchor device 100 in order to actuate the deployment pin 152. As described herein, other clamps or restraints may be used to keep the arms 120 and 122 from deploying before the position of the device is confirmed for deployment. The force arrows 156 and 158 are shown to illustrate this exemplary embodiment providing balanced forces for deploying, allowing a release of the arms 120 and 122 from the deployment pin 152 without significant movement of the device or significant force on the device relative to the bone. Alternate designs may be adapted to balance forces used in removing clamps or other restraints and otherwise reduce the unintended effects of forces and movements created by removing the restraints from the device 100 for deployment.

Achieving the required deployment properties with the described embodiments necessitates a deployment method that allows for easy and reliable insertion and deployment of the device across the bone interface. Imparting those forces along an axis of the pin 152 and pinhole 114 by way of a rigid device or external handle can impart unbalanced forces 160 that may tends to move the device with the pin or possibly twist the device within the prepared bone bores in the bone pieces. In other embodiments, deployment devices 100 are described herein without rigid interconnections for the sheathed deployment mechanism 150. Other restraining mechanisms may be adapted similarly to include direct access to the restraining portion of the device 100 (e.g., the pinhole 114), the need to balance the forces (e.g., 156 and 158) of removing the restraints, and the need to impart as few unbalanced forces 160 on the device as possible.

A sheathed pin deployment device and process add complications to the bone anchor system. However, using the sheathed pin (or dual pin) arrangement allows further refinements that are not directly related to the sheathed pin design. Further refinements include the ability to remove portions of the direct or rigid connection between the surgeon and the sheathed deployment pin mechanism 150, substituting a rigid connection requiring a significant pullout force (e.g., the upward arrow 156) to be balanced, while incorporating with a flexible cable to actuate the deployment pin 152, relative to the sheath 154.

In some embodiments of deployment mechanisms, only limited travel is configured to be allowed by the releasing mechanism (e.g., sheathed deployment pin mechanism 150). For example, a deployment pin 152 and a sheath 154, or a flexible cable needs only to apply the balanced forces over a limited distance in order to effectively remove the pin 152 and deploy the device 100. Therefore, the embodiment shown of the deployment pin 152 and the sheath 154 need not maintain a similar structure to that shown either above the device 100, along the sheath 154, or surrounding the entire pin 152. In other words, the balancing mechanism need not extend far beyond the device, and certainly need not extend as far as the actuation handle. These balanced forces 156 and 158 and actuations need only be created in the area of the device 100, as shown in this example of removing the deployment pin with the balanced forces. Therefore, multiple embodiments may be adapted using these principles as appropriate for the particular application.

Figure 9:
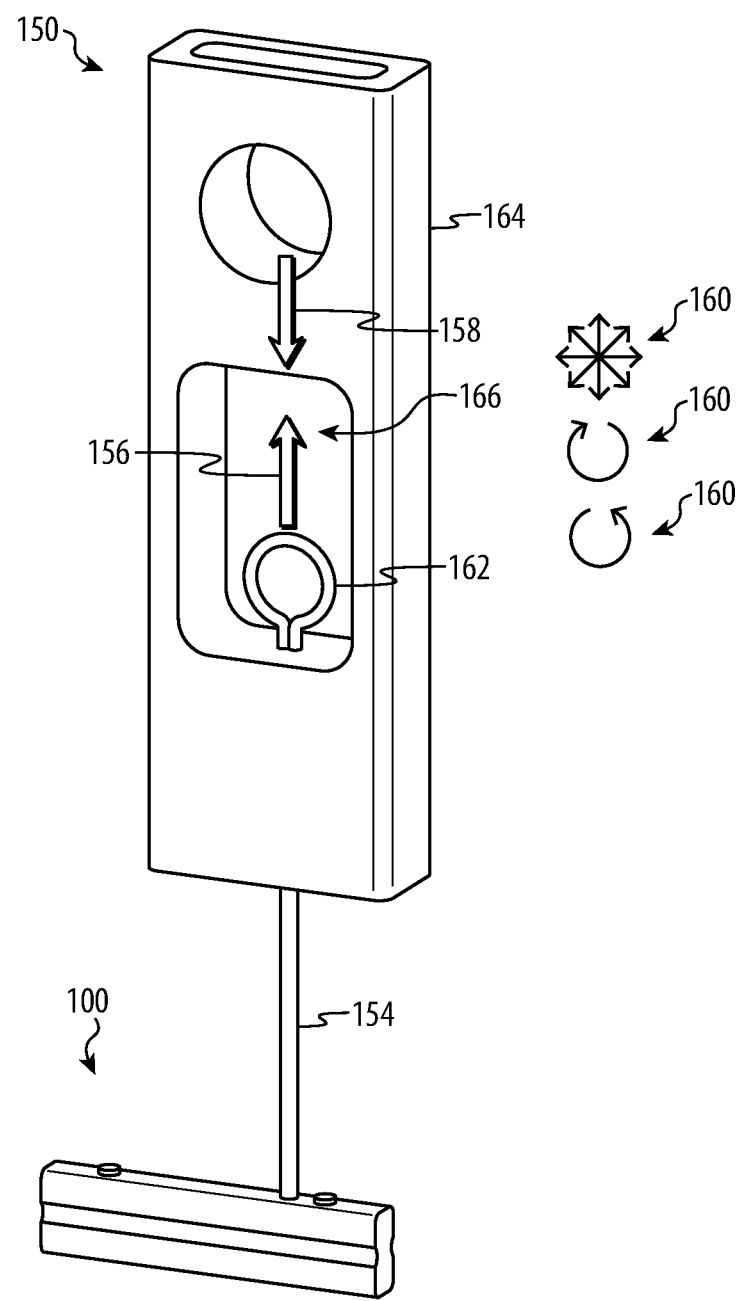
FIG. 9 shows an exemplary embodiment of a sheathed deployment pin mechanism for deploying the device by implementing a release of sheathed deployment pin.

FIG. 9 shows an exemplary embodiment of a sheathed deployment pin mechanism 150 for deploying the device 100 by implementing a release of sheathed deployment pin. The exemplary embodiment allows deployment of the device 100 via pushing the outside sheath 154 with the outer handle body 164 that is rigidly attached to the sheath 154. To compliment this action, the deployment technique includes pulling up on the eyelet 162. In the embodiment show, the eyelet 162 is accessible via a window 166 in the outer handle body 164, wherein the eyelet is that is rigidly attached to the deployment pin inside the device 100. This deployment techniques allows for the surgeon to balance forces 156 and 158. These balanced forces 156 and 158 are depicted by the arrows that are parallel to the arrows shown in FIG. 8.

The direct and/or rigid connections between the eyelet 162 and the deployment pin and between the outer handle body 164 and the sheath 154 creates the issue of requiring a surgical technique that provides the balanced forces 156 and 158 while not producing unbalanced forces 160 on the deployment pin mechanism 150 and the device 100. Therefore, this embodiment provides the deleterious opportunity to translate or rotate the device 100 relative to the bone pieces while in the process of creating the balanced forces 156 and 158 to deploy the device 100. As described further herein, the positioning and rotation of the device during insertion and deployment may have critical requirements and not allow margin for any significant translation or rotation of the device 100. These requirements for device immobility may be difficult to maintain if the forces are not further disassociated from the deployment tool's handle or other mechanism for operation by a surgeon.

Figure 10:
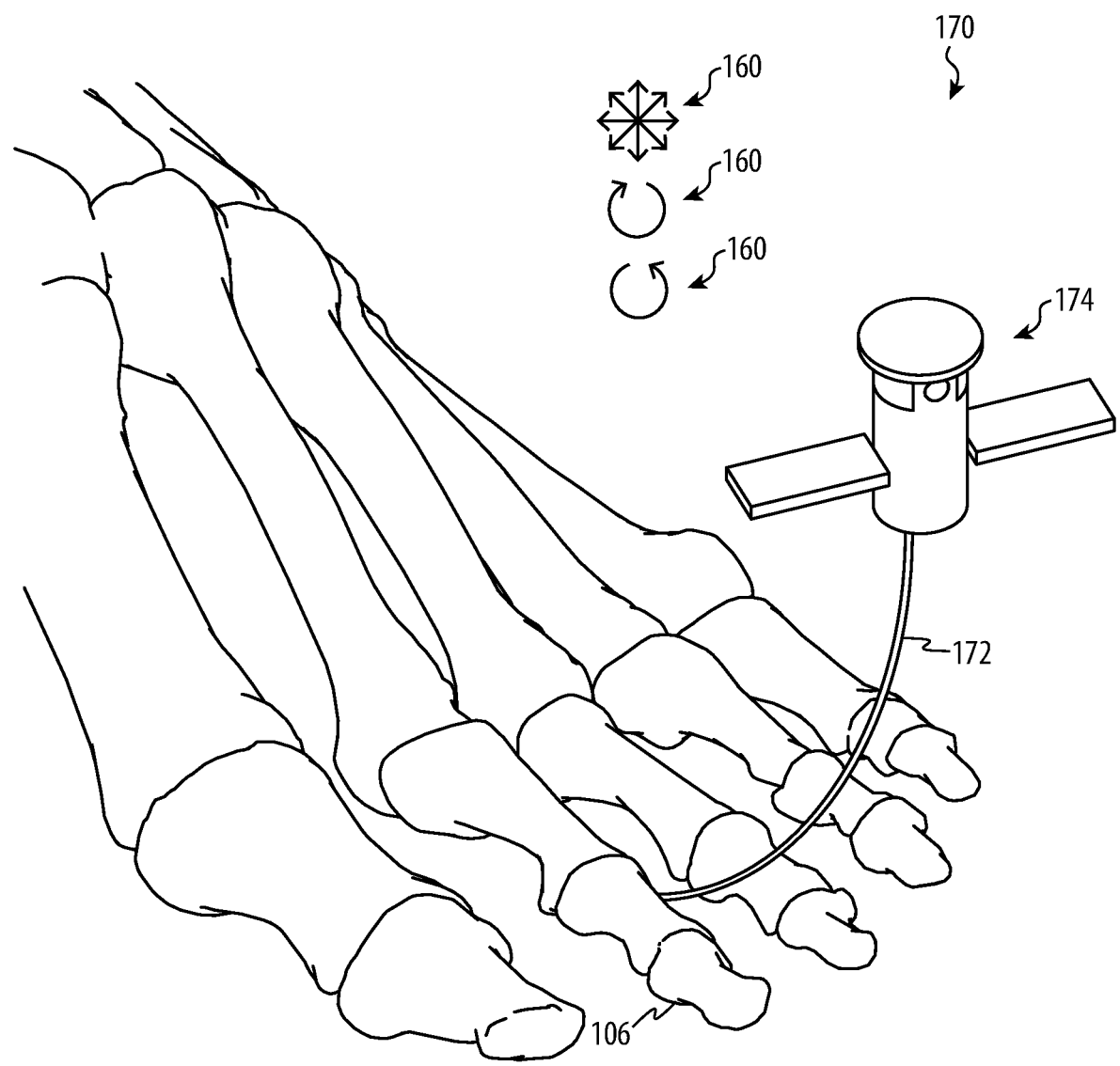
FIG. 10 shows an exemplary embodiment of a tethered deployment mechanism for removing a deployment pin from the pinhole in the device via a flexible cable.

FIG. 10 shows an exemplary embodiment of a tethered deployment mechanism 170 for removing a deployment pin from the pinhole in the device via a flexible cable 172. This embodiment uses a flexible cable 172 attached to the deployment pin for removing via a sheathed pin. The sheathed pin may be situated adjacent to the deployment pin, as described further herein, such as being placed within the flexible cable, surrounding the deployment pin partially, or fully surrounding the deployment pin. Removing this deployment pin deploys the device within the prepared PIP joint 106, also as described further herein. Attaching the sheathed deployment pin mechanism 170 to a flexible cable 172 further limits the possibility of transmitting unbalanced force(s) 160 between the handle 174 of the deployment mechanism 170 and the device, ideally only transmitting the balanced pin/sheath actuation forces, and reducing the chances of imparting additional unbalanced forces 160 through the flexible cable 172, such as unwanted twisting or translation forces to the device.

Using a flexible cable 172 may be substituted for another force-isolating mechanism that both allows for further accurate positioning of the device during insertion and deployment, while maintaining the device's ability to deploy with significant forces immediately upon removing the constraint from the arms of the device.

By additionally isolating the unintended forces from the device, the processes of surgical insertion and deployment of the device are optimized for accuracy. By choosing a suitably flexible cable 172 for the deployment mechanism 170, the process of positioning the device within the prepared joint 106 may be simplified as the handle 174 will not move the device within the bone bore before deployment via the balanced forces. The process of controlling deployment can then continue without significant chance of unbalanced forces 160 travelling from the handle 174 to the device and disturbing the inserted position of the device before or during its deployment.

It is clear that many modifications and variations of these embodiments can be made by one skilled in the art without departing from the spirit of the novel art of this disclosure. While specific parameters, including device configurations, parameters of components, and thresholds may have been disclosed, other reference points can also be used. These modifications and variations do not depart from the broader spirit and scope of the present disclosure, and the examples cited here are illustrative rather than limiting.

What is claimed is:

1. A bone anchor system, comprising:
    a bone anchor having a central portion disposed between at least two pivot points;
    a distal anchor element and a proximal anchor element situated on the bone anchor; and
    an actuation control mechanism configured for holding a stored strain in the central portion of the bone anchor, wherein the stored strain is configured to keep both the distal anchor element and the proximal in an aligned insertion configuration;
    wherein the actuation control mechanism is configured such that a release of the stored strain in the central portion by manipulating the actuation control mechanism, thereby rotates one or more bodies of the bone anchor around the at least two pivot points, and thereby rotates the distal anchor element and the proximal anchor element simultaneously outward about the at least two pivot points.

2. The bone anchor system of claim 1, wherein the distal anchor element or the proximal anchor element is contained in the central portion of the bone anchor.

3. The bone anchor system of claim 1, wherein the actuation control mechanism is situated on the one or more bodies of the bone anchor that rotate in response to manipulating the actuation control mechanism.

4. The bone anchor system of claim 1, wherein the actuation control mechanism is situated on the one or more bodies outside of the central portion of the bone anchor.

5. The bone anchor system of claim 1, wherein the stored strain in the central portion is stored by a super-elastically strained shape memory alloy at a storage temperature above an austenite finish temperature of the shape memory alloy.

6. A bone anchor system, comprising:
    a bone anchor for joining two bone pieces of one or more bones of a patient at an angle to an axis of the bone anchor;
    at least two anchor elements each for extending into one of the two bone pieces of the patient, the at least two anchor elements rotationally connected via a connection spanning at least two rotational pivot points forming a central portion of the bone anchor, the central portion including a shape memory alloy actuator made of a shape memory alloy with a selected austenitic finish temperature of the shape memory alloy selected such that the martensitic crystalline phases of the shape memory alloy are unstable at 20 degrees Celsius;
    wherein the at least two anchor elements are configured to be actuated about the at least two rotational pivot points away from the axis in response to a release of strain in the shape memory alloy actuator of the central portion of the bone anchor; and
    an actuation control mechanism configured for holding the strain in the shape memory alloy actuator of the central portion of the bone anchor;
    wherein the actuation control mechanism is further configured such that a release of the strain in the shape memory alloy actuator of the central portion by manipulating the actuation control mechanism rotates the at least two anchor elements around the at least two rotational pivot points.

7. The bone anchor system of claim 6, wherein the actuation control mechanism is further configured to release strain in the shape memory alloy actuator of the central portion of the bone anchor, thus rotating each of the at least two anchor elements simultaneously with a single action of the actuation control mechanism.

8. The bone anchor system of claim 6, wherein the at least two pivot points are in equal number to the at least two anchor elements.

* * * * *